United States Patent [19]

Hori et al.

[11] Patent Number: 5,464,420
[45] Date of Patent: Nov. 7, 1995

[54] COMPRESSIVE HEMOSTATIC BELT

[75] Inventors: Shinichi Hori, Sakai; Atsuko Kawasaki, Akashi; Takefumi Nakashita, Kobe; Yoshiharu Inui, Takarazuka; Toshiaki Sakaki, Kakogawa; Miyo Miki, Kobe, all of Japan

[73] Assignee: Sumitomo Rubber Industries, Ltd., Kobe, Japan

[21] Appl. No.: 206,255

[22] Filed: Mar. 7, 1994

Related U.S. Application Data

[63] Continuation of Ser. No. 906,341, Jun. 30, 1992, abandoned.

[30] Foreign Application Priority Data

Feb. 6, 1992 [JP] Japan ................................ 4-020793
Apr. 22, 1992 [JP] Japan ................................ 4-102850
Apr. 22, 1992 [JP] Japan ................................ 4-102851

[51] Int. Cl.$^6$ ........................................ A61B 17/00
[52] U.S. Cl. ........................................ 606/202
[58] Field of Search ..................... 606/201–204; 128/667, 686, 682

[56] References Cited

U.S. PATENT DOCUMENTS

| | | | |
|---|---|---|---|
| 3,171,410 | 3/1965 | Towle, Jr. et al. | 606/202 |
| 3,625,219 | 12/1971 | Abrams et al. | 606/203 |
| 3,670,735 | 6/1972 | Hazlewood | 128/327 |
| 4,275,718 | 6/1981 | Jungmann | 128/95 |
| 4,800,900 | 1/1989 | French | 606/202 |
| 4,829,994 | 5/1989 | Kurth | 606/203 |

FOREIGN PATENT DOCUMENTS

| | | |
|---|---|---|
| 0462088 | 12/1991 | European Pat. Off. . |
| 514026 | 11/1992 | European Pat. Off. . |
| 910340 | 6/1946 | France . |
| 1388162 | 12/1964 | France ................... 606/203 |
| 56336 | 5/1891 | Germany . |
| 571744 | 3/1933 | Germany . |
| 3333311 | 4/1985 | Germany . |
| 4012974 | 10/1991 | Germany . |
| 1206605 | 10/1967 | United Kingdom . |

Primary Examiner—Stephen C. Pellegrino
Assistant Examiner—William Lewis
Attorney, Agent, or Firm—Nikaido, Marmelstein, Murray & Oram

[57] ABSTRACT

The invention presents a compressive hemostatic belt which is easy to handle and is disposable. A balloon 5 inflatable by filling with fluid is mounted on a specific position of a strip 1 made of non-elastic or low-elastic fiber cloth or the like through mounting means, and a pump 8 and a pressure gauge 9 are connected to the balloon 5 through a check valve 6. The balloon 5 is filled with a fluid by manipulating the pump 8 while observing the pressure gauge 9 to inflate the balloon 5, so that only the area where bleeding is to be stopped is put under pressure. Since the balloon 5 is inflated only on the specified area, a piece of hard material 4 may be placed between the balloon 5 and the strip 1. A non-elastic reinforcing member 11 inserted on the opposite side of the balloon 5 can be varied, or the confronting portion of the strip 1 against the balloon 5 can be formed of a non-elastic reinforcing member stronger than the materials of other portions of the strip.

6 Claims, 2 Drawing Sheets

COMPRESSIVE HEMOSTATIC BELT

This application is a continuation of application Ser. No. 07/906,341 filed Jun. 30, 1992, now abandoned.

BACKGROUND OF THE INVENTION

1. Field of the Invention

The present invention relates to a compressive hemostatic belt used to stop bleeding from a catheter insertion wound upon completion of an arterial catheter examination.

2. Prior Art

Recently, arterial catheter examinations have been made for contrast medium-using diagnosis of hearts or cerebral blood vessels. Cardiac catheter examinations are made by surgical operation in a few cases but in most cases by the so-called catheter puncture method where a catheter is moved from the femoral artery or vein in the inguinal region, to the heart.

In this examination method, a contrast medium or various medicines are injected through the catheter puncturing the femoral artery or vein in the inguinal region or various preoperative and postoperative examinations are conducted. In this connection, there is a need to compress the catheter insertion wound for a relatively long time in order to stop bleeding from the catheter insertion wound owing to extraction of the catheter from the femoral artery or vein in the inguinal region.

As for such compressive hemostatic methods for catheter insertion wounds, it has been common practice for a doctor or nurse to manually compress a catheter insertion wound for about 15 minutes, apply gauze to the catheter insertion wound, apply 3 or 4, 70-cm long 5-cm wide fabric adhesive plasters over said gauze to compress the catheter insertion wound from above the gauze, placing a sand bag having a controlled weight of 500–1000 kg, and fix the sand bag against moving by the fabric adhesive plaster, such fixed state being maintained for 12–24 hours.

However, in the conventional method described above, the use of adhesive plaster as means for fixing the gauze applied to the catheter insertion wound and also fixing the sand bag placed thereon after extraction of the catheter causes such drawbacks to the patient as a stiffening feel, pain and itch, and favors the development of dermatitis and vesicular exanthema.

The sand bag tends to slip off when the patient lying on his back tilts his body even slightly, and such deviation of the sand bag results in the sand bag deviating from the compressed area, making the hemostatic effect imperfect, and thereby leading to other drawbacks, such as ecchymoma.

On the other hand, in order to solve said problems, Japanese Patent Application Disclosure No. 92746/1985 or Japanese Patent Application Disclosure No. 198139/1985 suggests a compressive hemostatic belt formed of stretch fabric as means for compressive hemostatic means for catheter insertion wounds to replace the adhesive plaster and sand bag.

Such a compressive hemostatic belt, however, is constructed to make it difficult for a user to wrap it and to visually ascertain the level of its compressive force on the catheter insertion wound and makes it necessary for him to rewrap it when adjusting the compressive force; thus, the loading state of the belt is unstable.

Further, since the belt uses an expensive stretch textile fabric, its production cost is very high, making it difficult to throw after use when there is a hygienic problem of causing infectious diseases due to the adhesion of blood. Therefore, to prevent such hemoinfectious diseases, after each use of the compressive hemostatic belt, it has to be washed and sterilized, imposing limitations not only from a hygienic standpoint but also from the standpoint of enhancing labor saving for nurses.

SUMMARY OF THE INVENTION

To solve the above problems, the present invention is characterized by installing a balloon inflatable with fluid by fitting means at a specified position on a strip of non-elastic or low-elastic fiber cloth. By filling the balloon with the proper type of fluid applicable to the circumstances, the balloon can be inflated to put pressure on an area where bleeding is to be stopped.

To prevent the balloon from inflating to the side opposite to the area where bleeding is to be stopped, a piece of hard material is placed between the balloon and the strip, or a non-elastic reinforcing member is integrally applied on the side of the balloon confronted by the strip, or the balloon is formed thick at the side confronting the strip, and thin at the side confronting the area where bleeding is to be stopped.

By placing a piece of hard material between the balloon and the strip, the balloon is inflated only ton and the area where bleeding is to be stopped while preventing inflation to the side opposite to that area.

By applying a non-elastic reinforcing member on the side of the balloon confronted by the strip, the balloon can be inflated only to the area where bleeding is to be stopped while preventing inflation to that side opposite to the area, without using a piece of hard material.

By varying the thickness of the balloon so as to be thick at the side confronted by the strip and thin at the side confronted by the where bleeding is to be stopped, without using hard material, the balloon can be inflated only to that area while preventing inflation to the side opposite to the area, without using and hard material.

In another embodiment, to prevent the balloon from inflating to the side opposite to the stopping area, at least the portion of the strip confronted by the balloon is made of a non-elastic reinforcing member made of material stronger than that of the other portions. As a result, without using any hard material, the balloon can be inflated only to the area where bleeding is to be stopped while preventing inflation to that side opposite to the area.

In a different embodiment, to prevent the balloon from inflating to the side opposite to the area where bleeding is to be stopped, plural non-elastic reinforcing fiber cloth pieces are overlaid at least in the portion of the strip confronting the balloon. As a result, without using any hard material, the balloon can be inflated only to the area where bleeding is to be stopped while preventing inflation to the side opposite to that area.

In the present invention, a fluid feed pump and a pressure gauge are detachably installed in the balloon through a check valve. Therefore, while observing the pressure gauge, the pump may be manipulated to fill the balloon with fluid to pressure the area where bleeding is to be stopped.

According to the invention, since the strip is composed of non-elastic or low-elastic fiber cloth or the like, the development of a stiffening feel, pain or itch can be avoided and dermatitis and bubbles are prevented. The use of the balloon which is expanded by being filled with fluid as pressure means provides a narrower range of pressure, ensuring a hemostatic function for pressuring only a catheter insertion wound while causing almost no pressure feeling to be transmitted to the other areas.

In addition, by composing a loading structure by connecting a pump and a pressure gauge through a check valve to a balloon that can be inflated by filling with fluid, any pressure desired to be applied to the catheter insertion wound may be freely adjusted, and the adjusted pressure may be maintained for a long time by the check valve.

Besides, since hemostatic compressing and fixing are achieved simultaneously by the balloon that can be inflated by being filled with fluid, there is provided a compressive hemostatic belt whose operability is satisfactory and which does not require any sand bag or the like and is compact and easy to carry about.

Furthermore, the constituent members excluding the pump and pressure gauge are much cheaper than conventional parts, allowing the belt to be thrown away once it has been used; thus, noteworthy effects from the standpoint of improving health control and promoting labor saving are attained.

The invention employs the balloon which is inflated largely only at the side opposite to a wounded part and not inflated so much on the outer side, requiring no hard case. The pressure means comprises only an elastic balloon, posing no problem when it is wound on the body, and enabling to provide the belt of this invention at a lower price where the disposable use of it pays.

In the invention, moreover, as the portion of the band confronting the balloon is strengthened to prevent the balloon from inflating to the opposite side of the area where bleeding is to be stopped, no hard case is required. The pressure means comprises only an elastic balloon which posses no problem when it is wound on the body, enables the providing of belt of this invention at a lower price where its disposable use becomes economical, and which does not add to the burden of environmental pollution.

DESCRIPTION OF THE PREFERRED EMBODIMENTS

Figure 1:
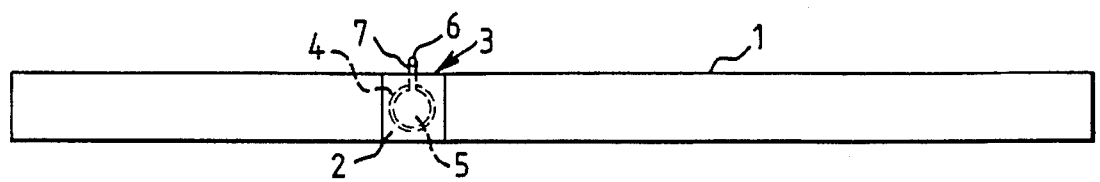
FIG. 1 is a front view showing a first embodiment of the invention.

Referring now to the drawings, some of the preferred embodiments of the invention will be described in detail below.

Figure 2:
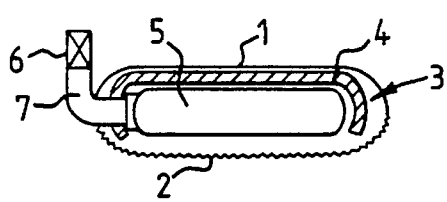
FIG. 2 is a longitudinal sectional view at the pocket position in the first embodiment.

FIGS. 1 and 2 show a first embodiment of the invention, in which numeral 1 denotes a strip composed of a non-elastic or low-elastic fiber cloth, and a pocket 3 is formed by sewing a pocket cloth 2 made of an elastic woven cloth on a specified position of the strip 1. Numeral 4 is a hard case made of a hard material such as synthetic resin formed in a cup form, and it is put in the pocket 3 of the strip 1 with the opening side directed to the pocket cloth 2. Numeral 5 is a rubber-made balloon which is inflated when filled with a fluid (air, nitrogen gas, carbon dioxide or other gas, or a liquid including a gel applicable to the circumstances), and it is put in the hard case 4 with a fluid feed tube 7 possessing a check valve 6 projected outside of the pocket 3 of the strip 1. To the fluid feed tube 7 of this balloon 5, for example, a manually-operated pump 8 and a pressure gauge 9 are connected, and by manipulating the pump 8 while observing the pressure gauge 9, the balloon 5 is filled with fluid through the fluid feed tube 7, so that the balloon 5 may be inflated.

To procedure of using the belt as a tourniquet for the invention is described below.

Figure 3:
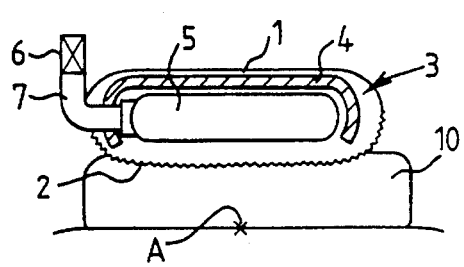
FIG. 3 is a longitudinal sectional view at the pocket position showing the state of use of the first embodiment.

As shown in FIG. 3, a piece of gauze 10 is put on a catheter insertion wound A after removing the catheter, the pocket piece 2 of the pocket 3 containing the balloon 5 is put thereon, directed to the gauze 10 side, and the strip 1 is wound around the waist of the patient by one turn or more, and its end portion is fixed by using fixing means such as adhesive plaster to wind around the body of the patient.

Figure 5:
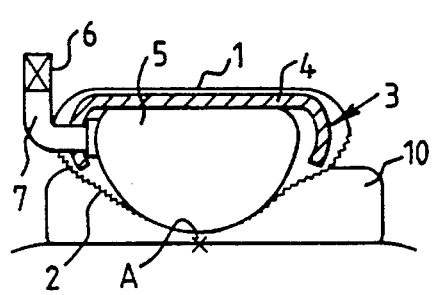
FIG. 5 is a longitudinal sectional view showing the state of pressuring the wound in the first embodiment.

When winding of the strip 1 is over in this manner, the manually-operated pump 8 and pressure gauge 9 are connected to the fluid feed tube 7 of the balloon 5, and the pump 8 is manipulated while observing the pressure gauge 9 to fill the balloon 5 with fluid, so that the balloon is inflated at the catheter insertion wound A side while restricting the inflation to the opposite side of the catheter insertion wound A by the hard case 4 as shown in FIG. 5, and the catheter insertion wound A is oppressed through the gauze 10 while fixing the strip 1 firmly to the patient.

When liquid is used as the fluid for inflating the balloon 5, as compared with gas, it hardly escapes the balloon 5 and the connected check valve 6, and if leaking, the strip 1 or other parts become wet so that the escape may be known immediately, and it is easy to keep constant the force of compression.

Thus, in the belt used for a towniquet, since the catheter insertion wound A is compressed by making use of the expansion of the balloon, only the catheter insertion wound A can be compressed, and the sensation of compression is hardly propagated to other areas on the patient. Still more, by manipulating the pump 8 while observing the pressure gauge 9 depending on the physique of the patient, the filling degree of the balloon with fluid is adjusted, and the force of the compression applied to the catheter insertion wound A may be freely selected. The hemostatic action suited to the patient may be effected, while the selected force of compression may be maintained for a long time by the check valve 6. It is also possible to control the oppression force automatically, if necessary, by using a computer. In addition, since the strip 1 is made of non-elastic or low-elastic fiber cloth, it is free from stickiness, pain or itchiness, thereby preventing dermatitis or bulla.

When the entire strip 1 is formed in a bag by using non-elastic or low-elastic fiber cloth or the like, if the pocket 3 is made loose to allow inflation of the balloon 5, the oppression force to the catheter insertion wound A by inflation of the balloon 5 is sufficient. Alternatively, if the confronting side against the catheter insertion wound A of the pocket 3 accommodating the balloon 5 of the strip 1 is made of an elastic fiber, the compression force to the catheter insertion wound A is made secure.

In the first embodiment, the balloon 5 is incorporated in the pocket 3 of the strip 1 through a hard case 4 for suppressing the inflation to the opposite side of the catheter insertion wound A. Instead the balloon 5 may be exposed and placed in the pocket 3 of the strip 1. In this case, too, the balloon 5 is inflated to the catheter insertion wound A side while suppressing the inflation to the opposite side of the catheter insertion wound A side by the strip 1.

Figure 4:
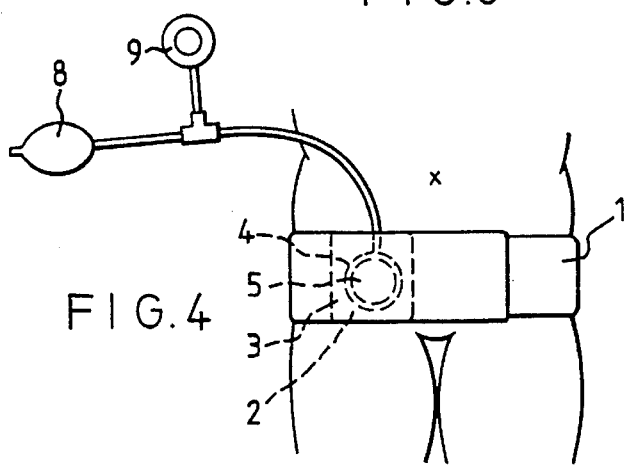
FIG. 4 is an explanatory diagram showing a winding example of belt.
Figure 16:
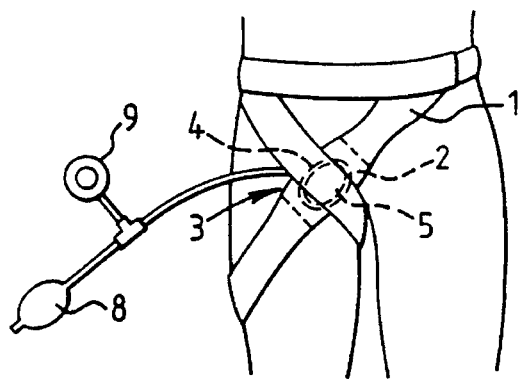
FIG. 16 is an explanatory diagram showing another winding example of the belt for tourniquet.

In the foregoing embodiment, as shown in FIG. 4, the strip 1 is wound around at right angle to the body axis, but the invention is not limited to this example. Aside from the winding manner in FIG. 4, for example, the strip 1 may be wound in an X-form as shown in FIG. 16. That is, the strip 1 can be pulled around from the inguinal part to the femoral outside part, femoral back part and femoral inside part, and from the hip joint pat to the femoral front side, and crossed in an X-form at the inguinal part. The remaining portion can be wound around the abdomen by one turn or more, and the end portion can be wound around by fixing with fixing means such as a nondirectional cloth fastener.

In this embodiment, a fiber cloth is used as the strip 1, but instead of fiber cloth, other non-elastic or low-elastic materials may be used such as leather and film. The pocket cloth 2 is made of elastic fiber cloth, and instead of this elastic fiber cloth, other elastic materials may be also used such as rubber.

The pocket may also be formed by forming a part of the strip 1 in a bag shape, in which the hard case 4 and balloon 5 may be incorporated.

In the first embodiment, incidentally, since the inflation of the balloon 5 to the opposite side of the catheter insertion wound A is prevented by means of the hard case 4, when the strip 1 is wound around the body, the hard case 4 may contact with the body, which may be felt uncomfortable. Accordingly, to prevent inflation of the balloon 5 to the opposite side of the catheter insertion wound A, the invention presents second to fifth embodiments as described below.

Figure 6:
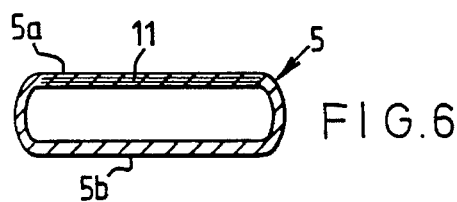
FIG. 6 is a longitudinal sectional view of a balloon in a second embodiment of the invention.

First, in the second embodiment, the balloon 5 in the constitution of the first embodiment is structured as shown in FIG. 6. At the side of the balloon 5 confronting the strip 1, that is, at the outside 5a, a sheet of non-elastic reinforcing member 11 made of cloth, mesh, film, PET, paper or the like is inserted. The non-elastic reinforcing member 11 is integrally inserted in the outside 5a of the balloon 5 when manufacturing the balloon 5. In short, when manufacturing the balloon 5 in the latex immersion method, once the balloon die is immersed in latex and the non-elastic reinforcing member 11 is adhered to one side for forming the outside 5a of the balloon 5 of this balloon die, only the side of the balloon die adhered with the non-elastic reinforcing member 11 is immersed again in latex, and vulcanized, so that the non-elastic reinforcing member 11 is integrally inserted into the outside 5a of the balloon 5.

Figure 7:
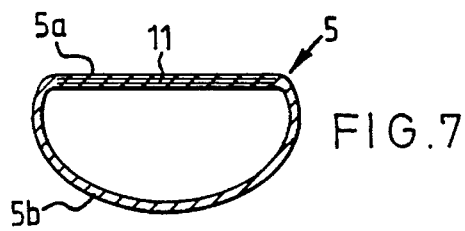
FIG. 7 is a longitudinal sectional view showing the state of inflation of the balloon in the second embodiment.
Figure 8:
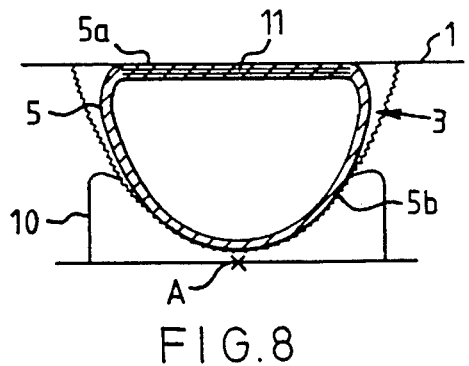
FIG. 8 is a longitudinal sectional view showing the state of pressuring the wound in the second embodiment.

In the second embodiment, when the balloon 5 is filled with fluid, as shown in FIG. 7, the outside 5a of the balloon 5 is not inflated due to the non-elastic reinforcing member 11, while only the side confronting the catheter insertion wound A, that is, the ailing side 5b, is inflated largely. Accordingly, as shown in FIG. 8, the balloon 5 is prevented from inflating the side opposite of the catheter insertion wound A. The balloon 5 is inflated on the catheter insertion wound A side, so that the catheter insertion wound A may be compressed with a sufficient force through the gauze 10.

Figure 9:
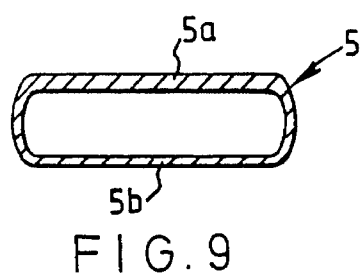
FIG. 9 is a longitudinal sectional view of a balloon in a third embodiment of the invention.

Next, in the third embodiment, the balloon 5 in the constitution of the first embodiment is structured as shown in FIG. 9. That is, the thickness of the balloon 5 is thin at the ailing side 5b, and thick at the outside 5a at a specific rate to the ailing side 5b. The thickness of the ailing side 5b is about 0.1 to 2.0 mm. If thinner, it may lead to problems such as pinholes, or aging or tearing in the course of storage or transportation. If thicker, it is difficult to fill with fluid or the force of compression is lowered as compared with the internal pressure. The thickness of the outside 5a is about 0.5 to 5.0 mm. For the same reason as above, and especially with a greater thickness, problems in the manufacturing method or the like may occur.

Figure 10:
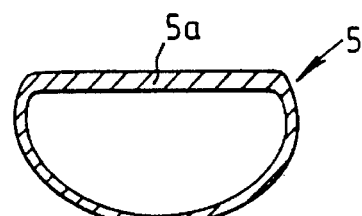
FIG. 10 is a longitudinal sectional view showing the state of inflation of the balloon in the third embodiment.
Figure 11:
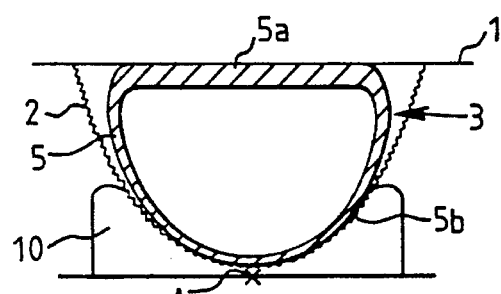
FIG. 11 is a longitudinal sectional view showing the state of pressuring the wound in the third embodiment.

In the third embodiment, if the balloon 5 is filled with fluid, the outside 5a of the balloon 5 is not inflated so much because of the great thickness as shown in FIG. 10, while the ailing side 5b is thin and is primarily inflated. As a result, as shown in FIG. 11, the balloon 5 is prevented from inflating on the side opposite of the catheter insertion wound A. It is inflated only on the catheter insertion wound A side, so that the catheter insertion wound A maybe compressed with a sufficient force through the gauze 10.

Thus, in the second and third embodiments, without using the hard case 4 as in the first embodiment, the discomfort due to contact with the hard case 4 with the body when wound around the body experienced in the first embodiment is eliminated. The cost for disposal may also be lowered, so that it may be presented at a lower cost.

Figure 12:
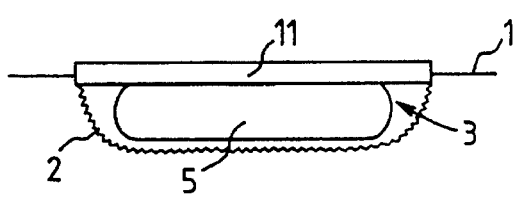
FIG. 12 is a longitudinal sectional view showing the portion of a band confronting the balloon in a fourth embodiment of the invention.

In the fourth embodiment, the strip 1 in the constitution in the first embodiment is structured as shown in FIG. 12. The portion of the strip 1 confronting the balloon 5, that is the adhering portion of the pocket cloth 2, is made of a non-elastic reinforcing member 11 composed of fiber cloth stronger than the fiber cloth forming the other portions. (e.g. fiber cloth for judo clothes), leather, vinyl, or the like.

Figure 13:
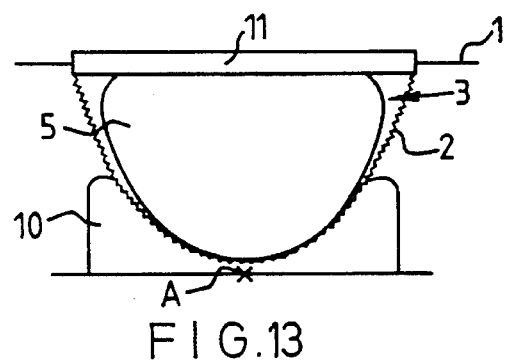
FIG. 13 is a longitudinal sectional view showing the state of pressuring the wound in the fourth embodiment.

In the fourth embodiment, when the balloon 5 is filled with fluid, since the confronting part of the strip 1 to the balloon 5 is made of non-elastic reinforcing member 11, as shown in FIG. 13, the balloon 5 is prevented from inflating to the side opposite of the catheter insertion port A by the non-elastic reinforcing member 11, and is inflated primarily toward the catheter insertion wound A side. Accordingly, the catheter insertion wound A may be compressed with a sufficient force through the gauze 10.

In this embodiment, only the confronting portion of the strip 1 against the balloon 5 is formed of non-elastic reinforcing member 11, but the entire strip 1 may be formed of the non-elastic reinforcing member 11.

Figure 14:
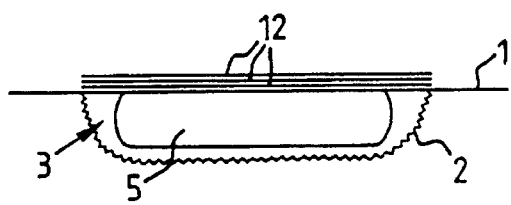
FIG. 14 is a longitudinal sectional view showing the portion of a band confronting the balloon in a fifth embodiment of the invention.

Next, in the fifth embodiment, the strip 1 in the constitution in the first embodiment is structured as shown in FIG. 14. The confronting portion of the strip 1 to the balloon 5, that is the adhesion portion of the pocket 2, is increased in strength higher than in other portions by overlaying a plurality of non-elastic reinforcing fiber cloths 12, 12 - - - .

Figure 15:
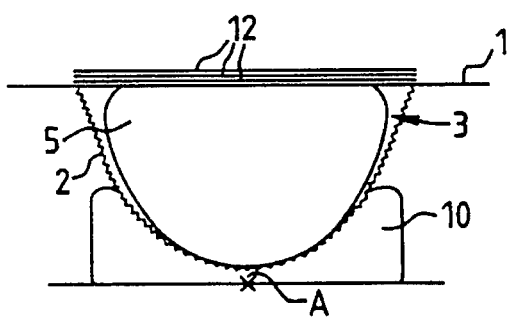
FIG. 15 is a longitudinal sectional view showing the state of pressuring the wound in the fifth embodiment.

In the fifth embodiment, when the balloon 5 is filled with fluid, since the confronting portion of the strip 1 against the balloon 5 is increased in strength by overlaying the plurality of non-elastic reinforcing fiber cloth 12, 12, - - - , as shown in FIG. 15, the balloon 5 is prevented from inflating the side opposite of the catheter insertion wound A by the non-elastic fiber cloth reinforcements 12, 12, - - - , and is inflated primarily on the catheter insertion wound A side. Accordingly, the catheter insertion wound A may be compressed with a sufficient force through the gauze 10.

In this embodiment, the plurality of non-elastic reinforcing fiber cloths 12, 12, - - - are overlaid only on the confronting portion of the strip 1 against the balloon 5, but the plurality of non-elastic reinforcing fiber cloths 12, 12, - - - may be overlaid on the entire strip 1.

Thus, in the fourth and fifth embodiments, since the hard case 4 as in the first embodiment is not used, when wound on the body, the discomfort due to contact of the hard case 4 of the first embodiment with the body is eliminated. Also the cost is lowered for disposal, so that it is possible to present at a lower cost, and not contribututing to environmental pollution because of its spontaneous degradability when discarded by burning or burying.

In the foregoing embodiments, fiber cloth is used as the strip 1, but instead of the fiber cloth, leather or film or other non-elastic or low-elastic material may be used. The pocket cloth 2 is made of elastic fiber cloth, but instead of the elastic fiber cloth, rubber or other elastic material may also be used.

What is claimed is:

1. A compressive hemostatic belt system, comprising:

a mounting strip for binding a patient, said strip being formed from at least one of a non-elastic and a low-elastic material;

a balloon mounted in said strip and positioned so as to compress a selected area of the body of the patient when inflated, said balloon having means for inflating said. balloon with fluid; and inflation directing means mounted with said balloon, for directing inflation of said balloon substantially only toward the selected area of the body and for preventing inflation away from the body, wherein said mounting strip includes a pocket holding said balloon and said inflation directing means, the pocket being formed with a contact side part formed from an elastically expandable sheet material and positioned so as to contact with the selected area of the body of the patient.

2. A compressive hemostatic belt system as claimed in claim 1, wherein said inflation directing means includes a hard case member positioned on an outer side surface of said balloon so as to prevent inflation of the outer side of said balloon and to induce inflation of substantially only an inner inflating side of said balloon.

3. A compressive hemostatic belt system as claimed in claim 1, wherein said inflation directing means includes a non-elastic reinforcing sheet member positioned on an outer side surface of said balloon so as to prevent inflation of the outer side of said balloon and to therein induce inflation of substantially only an inner inflating side of said balloon.

4. A compressive hemostatic belt system as claimed in claim 1, wherein said inflation directing means is formed as an outer side surface of said balloon having a thickness greater than an inner inflating side of said balloon so as to prevent inflation of the outer side of said balloon and to therein induce inflation of substantially only the inner inflating side of said balloon.

5. A compressive hemostatic belt system as claimed in claim 1, wherein said inflation directing means includes a non-elastic reinforcing member positioned on an outer side surface of said balloon so as to prevent inflation of the outer side of said balloon and to therein induce inflation of substantially only an inner inflating side of said balloon, the non-elastic reinforcing member being formed from a plurality of non-elastic fibrous sheet layers.

6. A compressive hemostatic belt system as claimed in claim 1, further comprising:

a fluid feed pump with a pressure gauge detachably connected to said balloon through a check valve.

* * * * *